United States Patent [19]

Golimowski et al.

[11] 4,302,314
[45] Nov. 24, 1981

[54] VOLTAMMETRIC CELL, MEASURING ELECTRODE AND METHOD

[75] Inventors: Jerzy Golimowski, Warsaw, Poland; Laszlo Sipos, V. Gorica, Yugoslavia; Paul Valenta, Aachen, Fed. Rep. of Germany

[73] Assignee: Kernforschungsanlage Jülich Gesellschaft mit beschränkter Haftung, Jülich, Fed. Rep. of Germany

[21] Appl. No.: 136,932

[22] Filed: Apr. 3, 1980

[30] Foreign Application Priority Data

Apr. 7, 1979 [DE] Fed. Rep. of Germany ....... 2914193

[51] Int. Cl.³ ............................................. G01N 27/28
[52] U.S. Cl. ................................................. 204/195 R
[58] Field of Search .............. 204/1 T, 195 R, 195 M, 204/195 T, 195 H

[56] References Cited

U.S. PATENT DOCUMENTS

| | | | |
|---|---|---|---|
| 2,208,023 | 7/1940 | Ellis | 204/195 R |
| 3,484,359 | 12/1969 | Greene et al. | 204/195 R |
| 3,498,888 | 3/1970 | Johansson | 204/195 T |
| 3,523,070 | 8/1970 | Silverman et al. | 204/195 R |
| 3,562,130 | 2/1971 | Hoole et al. | 204/195 M |
| 3,657,093 | 4/1972 | Farren | 204/195 M |
| 3,859,193 | 1/1975 | Bednarski et al. | 204/195 H |
| 3,867,273 | 2/1975 | Gilbert | 204/195 M |
| 4,138,322 | 2/1979 | Barnes et al. | 204/195 H |
| 4,172,777 | 10/1979 | Yamamoto et al. | 204/195 M |
| 4,201,646 | 5/1980 | Matson | 204/195 H |

OTHER PUBLICATIONS

"Disc and Ring Rotating Electrodes", Data Sheet of Tacussel Electronique, (1976).
"Polarecord", Data Sheet of Deutsche Metrohm GmbH & Co., (1975).

*Primary Examiner*—G. L. Kaplan
*Attorney, Agent, or Firm*—Karl F. Ross

[57] ABSTRACT

A voltammetric cell, particularly for the determination of trace elements in a liquid, such as water, comprises a cover in which the measuring electrode and a reference electrode are mounted and which sealingly engages the cell vessel so that the contents of the latter will be sealed from contamination by the environment during the measuring process. The exchangeable meauring electrode has an analysis cup or crucible within the vessel into which the electrode can be inserted, the bottom of the vessel having a configuration complementary to the external configuration of the replaceable crucible or cup. The cup may have a downwardly tapering frusto-conical configuration and the base of the vessel can have a corresponding downwardly tapering recess accommodating at least the bottom of the cup.

4 Claims, 5 Drawing Figures

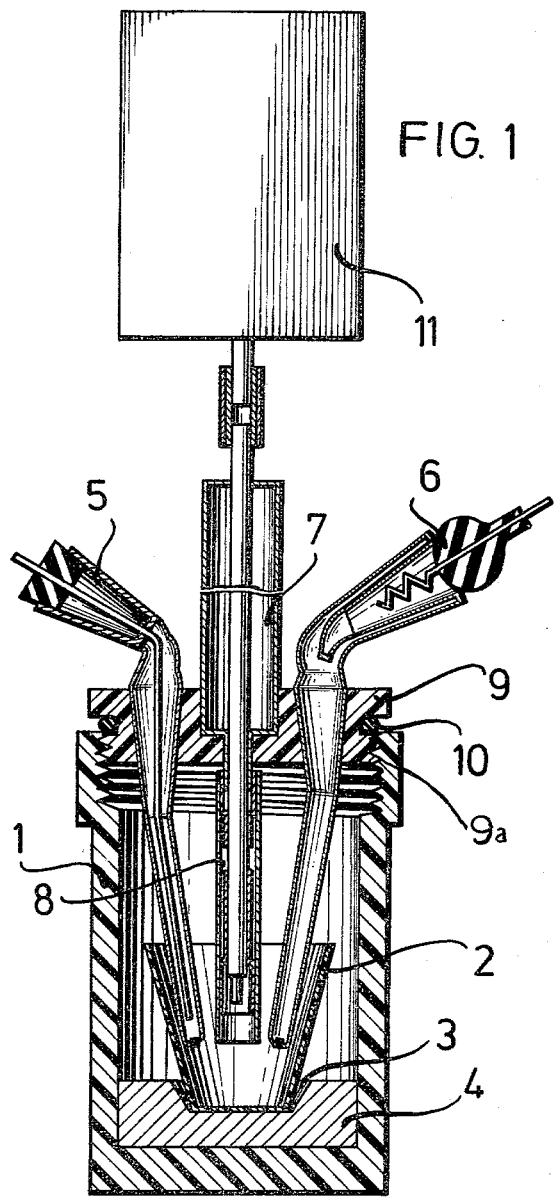

VOLTAMMETRIC CELL, MEASURING ELECTRODE AND METHOD

FIELD OF THE INVENTION

Our present invention relates to voltammetric measuring devices and, more particularly, to an improved voltammetric cell.

BACKGROUND OF THE INVENTION

Voltammetric cells, using electrochemical techniques for analysis, generally comprise a vessel receiving the solution to be evaluated, a reference electrode which has at least its tip immersed in the solution and a measuring electrode. The electrodes are connected to a variable potential or voltage source and generally to a recorder for recording the electrical response of the cell to the voltage change or some other parameter.

The electrodes may be mounted upon a cover which can be applied to the top of the cell.

Trace analysis for toxic substances in the environment, for example, require analytical methods and devices having high sensitivity, precision and accuracy. For the determination of the level of environmentally toxic substances, therefore, such as heavy metals, herbicides, fungicides and insecticides, voltammetric methods have been developed because they fulfill these requirements.

In various fields, for example analysis of sea water, drinking water and fresh water sources, voltametric methods of determining toxic compounds have been found to be preferable over other methods.

Naturally, because voltammetric methods are extremely sensitive, there is frequently the risk of contamination of the measuring vessel, of the cell, or of the measuring electrode with environmental contaminants which may not originally be present in the sample and which may be transferred to the cell during manipulation of the latter and/or during the normal operations in preparing the cell for an analytical run. These contaminants may arise from the atmosphere surrounding the cell, e.g. as the sample is introduced, or upon introduction of the electrodes or in some other similar manner.

Thus, relatively expensive apparatus was heretofore required to minimize the problem of environmental contamination and to keep the cell as free as possible from such contaminants during all phases of the operation.

Among other techniques for minimizing contamination was the use of vessels to receive the sample which were constituted of polytetrafluoroethylene or quartz.

Frequently there was also a desire to replace the measuring electrode for such cells either because a different type of measuring electrode was required or the original one became defective for some reason. This need was frequently incapable of being met in prior-art voltammetric systems because of the necessity to keep the cell free from contaminants and the danger that electrode replacement could introduce contaminants.

When the electrode was replaceable, however, the system was inordinately complex, expensive and otherwise disadvantageous.

For example, commercially available voltammetric cells (Tacussel) with replaceable measuring electrodes comprised a cover with a passage for the measuring electrode, the cell being also composed generally of quartz glass and having the auxiliary or reference electrode fused thereto, as well as a device for thermostatically controlling the temperature of the sample, for introducing a gas into the sample, etc. Such cells are difficult to clean and are so expensive that neither the cover nor the cell vessel can be considered to be "disposable" as is particularly desirable for high sensitivity measurements.

There are, however, also available cells (Methrohm) which are easier to clean and which have, for example, a cover provided with openings in which each of the elements normally mounted in the cover can be fitted.

In this system, the cover fits upon a conical vessel and is held in place by a clamping bail or lever. Even these systems are highly expensive, ill-affording the luxury of one-time use, although they do provide advantages from the point of view of simpler cleaning and rapid closure.

OBJECTS OF THE INVENTION

It is the principal object of the present invention to provide an improved voltammetric analysis cell, especially for a wide range of trace analyses under different conditions, which is relatively inexpensive and easy to clean, and thereby eliminates the disadvantages of prior-art systems, e.g. as mentioned above.

Another object of this invention is to provide a voltammetric cell with replaceable measuring electrodes so that the cell is more versatile than earlier systems and can be more flexibly adjusted to particular trace analysis.

Still another object of the invention is to provide an improved measuring element for such a cell.

SUMMARY OF THE INVENTION

These objects and others which will become apparent hereinafter are attained, in accordance with the present invention, by providing a voltammetric cell which comprises a vessel, a cover sealingly engageable with this vessel and having the reference and measuring electrodes mounted therein together with other elements necessary for operation of the cell, the measuring electrode having an electrode coupling member connectable to the measuring electrode while a replaceable analysis cup, crucible or beaker is provided within the vessel and has its outer contour conforming to the contour of the bottom of the vessel.

The other "elements" which can be mounted upon the cover can include temperature measuring means such as a thermometer or temperature sensor means for introducing a gas into the vessel to blanket the measuring cup or crucible, and any other means facilitating the measurement.

The replaceable cup or crucible may be disposable and can have a frustoconical downwardly tapering configuration which is seated in a recess formed in the bottom of the vessel and which can be complementary to the bottom of the crucible or, in any event, is dimensioned to receive and center the cup or crucible.

The connection between the cover and the vessel, which may be cylindrical, can be formed by a bayonet joint or screw thread, while a seal is advantageously formed on the cover to cooperate with the upper edge or lip of the vessel.

Such a cell can thus be assembled rapidly, can be charged readily with the sample and can be closed quickly. It is unusually simple in construction and can be used for different types of measurements under different conditions. The parts which come in contact with the sample can be mass produced and discarded after a single use, if they are not to be cleaned while the vessel itself and the cover never contact the sample directly and hence can be cleaned from environmental contaminants easily without concern for especial techniques intended to remove traces of the sample previously examined.

The requirements for the measuring cup or crucible are not stringent and it can be composed of any material which does not affect the sample or the measurement. The fabrication of the cup is inexpensive since the latter does not have to carry any closure means or devices which participate in the measurement.

The base or bottom of the vessel can be formed by an insert properly shaped and introduced into the cylindrical vessel, this insert having a relatively massive structure so that it can serve as a temperature control element directly or by conduction for a heating or cooling source. This insert can also be replaceable, e.g. so that its recess can be shaped to accommodate differently shaped vessels.

According to another aspect of the invention, the connectable and replaceable measuring electrode can include a metal rod or tube forming a conductor between the sensitive element of the measuring electrode and a lead running to the measuring circuit, this conductor being encased in a hardenable synthetic resin substantially to the end of the member at which a disk or the like of the metal forming this sensitive material, i.e. of the electrode material, is bonded by means of a conductive adhesive.

The hardened body can then be turned or machined to the desired shape.

The synthetic resin encasing the conductive rod or tube is preferably a room-temperature hardenable unmodified solvent-free epoxy resin (especially Araldit-B manufactured by Ciba AG, Basel, Switzerland) which can be provided with a hardener and hardened at an elevated temperature.

The conductive adhesive can be E/Solder ACME, a product of Epoxy Produkte GmbH, Fürth, Germany. This epoxy-based adhesive has a high bonding strength and conductivity.

The electrode with its coupling shank and the conductive rod of the latter, to which the electrode material disk is attached, can be formed by coating the rod with a low-viscosity synthetic resin mass, thereby ensuring that the mass will be free from bubbles and will form a continuous homogeneous sheath around the rod.

Plastics-encased conductors have been used in similar applications in the past although in such cases the electrodes were not only comparatively expensive, but also had the disadvantage that discontinuities or contaminants could accumulate or develop in the interface between the electrode material and the support, leading to early inactivation and inoperability of the electrode.

BRIEF DESCRIPTION OF THE DRAWING

The above and other objects, features and advantages of the present invention will become more readily apparent from the following description, reference being made to the accompanying drawing in which:

FIG. 1 is an axial cross-sectional view, partly in diagrammatic form, illustrating a voltammetric cell according to the invention.

SPECIFIC DESCRIPTION

Figure 2A:
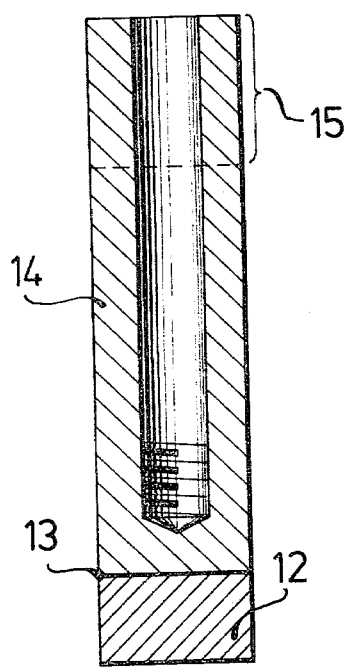
FIGS. 2a through 2d are diagrammatic axial cross sections illustrating successive steps in the formation of a measuring electrode which can be used in the cell of FIG. 1.

The voltammetric cell shown in FIG. 1 comprises a synthetic resin vessel 1 which is of an upwardly open cylindrical configuration, receiving a measuring cup or crucible 2 which contains the sample to be evaluated.

An insert disk 4, which can be metallic if it forms part of a temperature-control system, or a synthetic resin if temperature control by conduction through the disk is not required, is formed with a recess 3 dimensioned and shaped to accommodate the crucible or cup 2. The insert 4 can be removable from the vessel 1.

The auxiliary and reference electrodes 5 and 6 can be of conventional design and reach into the cup 2. A lead-in or guide tube 7 (ending just beneath the cover) is provided for the connectable and disconnectable measuring electrode 8.

The reference and measuring electrodes are thus mounted in a disk-shaped cover 9 which can form a bayonet or screw covering 9a with the mouth of the vessel 1. A seal 10, e.g. an O-ring, can be clamped between the cover 9 and the upper part edge of vessel 1.

The vessel 1 is, of course, composed of a material which is inert to any solvent used in the cell, while the crucible or cup 2 can be composed of quartz or polytetrafluoroethylene, but preferably can be simpler chemically inert material when the sample does not interact with the cup wall and cleaning of the cup is not desired. In this case, the cup or crucible can simply be discarded.

The crucible or cup should also be selected so that it can tolerate any chemical preparation of the sample which may be required, e.g. irradiation, solubilization or digestion.

The measuring electrode 8 can, of course, be replaced by another electrode having different electrode material, the electrode material being selected in the usual manner in accordance with the particular analysis undertaken. Such a replacement may also be desirable when the electrode is also of sufficiently low cost so as to be disposable.

A motor 11 is provided to rotate the electrode and is, as shown, connected to the measuring electrode which simultaneously serves as the stirrer.

The connector 7 can function as a bearing permitting rotation of the measuring electrode which can be connected by a sleeve ring to the measurement circuit (not shown) to which the auxiliary and reference electrodes 5 and 6 can also be connected.

Figure 2B:
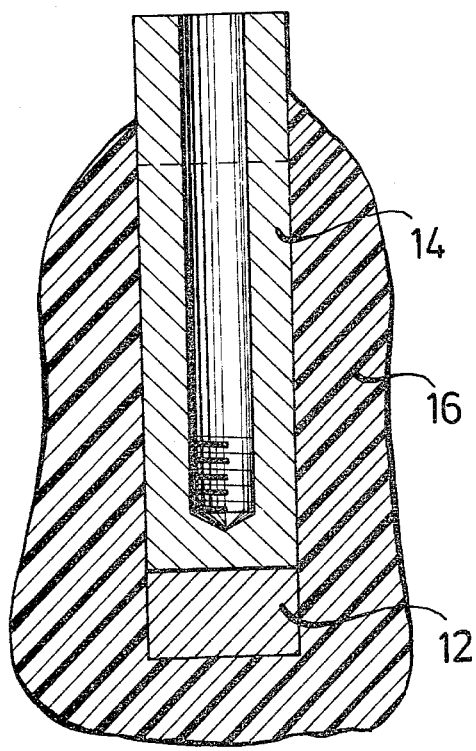
Figure 2C:
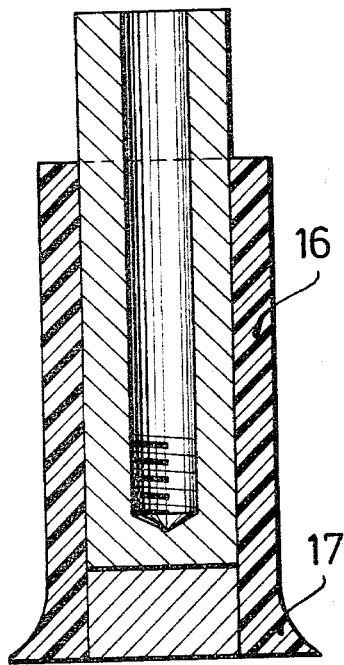

As can be seen from FIGS. 2a through 2c, a disk of the electrode material 12 is affixed by a layer of electrically conductive adhesive 13 (E-Solder ACME) to a rod 14 which forms the conductor as well as the connector to the electrode material. The rod 14 is composed of stainless steel and has a length sufficient to provide a portion 15 which can be held, engaged by a sleeve ring, received in a motor chuck or threaded onto a mandrel or shaft which is driven.

The assembly shown in FIG. 2a is then coated with an adherent hardenable synthetic resin by immersion in the low-viscosity liquid 16 for several minutes so that the hardening reaction occurs starting from the surface of the rod and electrode material and a synthetic clump having the shape shown in FIG. 2b is formed around the electrode. After hardening, the clump is shaped by machining (turning) the drop-shaped mass into the cylindrical sheet 16' shown in FIG. 2c, the lower end of the sheath flaring outwardly to improve the trace-material detectability by a factor of 2. The sheath is machined to expose the lower face of the electrode disk 12.

Figure 2D:
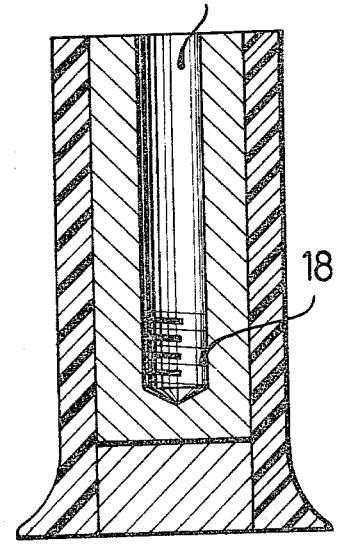

The electrode can also be sawn to the desired length as shown in FIG. 2d and provided with a thread 18 to accommodate a shaft 19. Experience has shown that such electrodes have practically no microscopic discontinuities or spaces at the edges of the disk, are more readily alignable and are less susceptible to inactivation than conventional electrodes.

We claim:

1. A voltammetric cell for analytical determination of trace materials in a liquid, comprising:
    an upwardly open vessel having a bottom;
    a cover sealingly engageable with the top of the vessel;
    a sample-receiving cup received in said vessel, said vessel having a bottom shaped to receive said cup;
    a measuring electrode having electrode material adapted to be in contact with said sample of said liquid to be held in said cup;
    a sealed rotary lead-in member for said measuring electrode, said member being disposed in said cover;
    an electrically conductive connecting member received in said lead-in member and forming an electrical connection with the electrode material in contact with a sample of said liquid in said cup, said measuring electrode being replaceably connected to said lead-in member;
    means for rotating said connecting member to rotate said measuring electrode in the sample of liquid in said cup; and
    at least one further electrode mounted in said cover and extending into the liquid sample in said cup.

2. The cell defined in claim 1 wherein said cup is a downwardly tapering frustoconical crucible and said vessel is provided with an insert forming its bottom and having an upwardly widening recess accommodating said crucible.

3. The cell defined in claim 1 or claim 2 wherein said connecting member comprises a conductive element bonded at its end to a disk of electrode material forming the measuring electrode with an electrically conductive adhesive, said disk and said element being surrounded by and bonded to a sheath of hardened synthetic resin, an end face of said disk being exposed to contact with said liquid sample and being flush with an end of said sheath.

4. The cell defined in claim 3 wherein said sheath is a unitary body of cylindrical configuration but divergent at said end of said sheath to its end face.

* * * * *